United States Patent
Ma

(10) Patent No.: US 10,953,060 B2
(45) Date of Patent: Mar. 23, 2021

(54) METHOD FOR EXTRACTION OF CHINESE HERBAL MEDICINE USING SMALL MOLECULE MICRO-SHEAR TECHNOLOGY

(71) Applicant: Jian Ma, Beijing (CN)

(72) Inventor: Jian Ma, Beijing (CN)

( * ) Notice: Subject to any disclaimer, the term of this patent is extended or adjusted under 35 U.S.C. 154(b) by 244 days.

(21) Appl. No.: 16/089,379

(22) PCT Filed: Apr. 28, 2016

(86) PCT No.: PCT/CN2016/080467
§ 371 (c)(1),
(2) Date: Sep. 28, 2018

(87) PCT Pub. No.: WO2017/166352
PCT Pub. Date: Oct. 5, 2017

(65) Prior Publication Data
US 2020/0297794 A1   Sep. 24, 2020

(30) Foreign Application Priority Data
Mar. 30, 2016   (CN) .......................... 201610190060.3

(51) Int. Cl.
*A61K 36/634* (2006.01)
*A61K 36/258* (2006.01)
*A61K 36/8888* (2006.01)

(52) U.S. Cl.
CPC .......... *A61K 36/634* (2013.01); *A61K 36/258* (2013.01); *A61K 36/8888* (2013.01); *A61K 2236/37* (2013.01)

(58) Field of Classification Search
None
See application file for complete search history.

(56) References Cited

FOREIGN PATENT DOCUMENTS

| CN | 1986029 | 6/2007 |
|---|---|---|
| CN | 101774890 | 7/2010 |
| CN | 102100732 | 6/2011 |
| CN | 104546948 | 4/2015 |
| CN | 104707047 | 6/2015 |

OTHER PUBLICATIONS

Wen et al., "Summary of Enzyme Applied in Extraction and Separation of Traditional Chinese Medicine", Guide of China Medicine, May 31, 2009, pp. 203-205.
Wu et al., "Exploration of Cell Wall Broken Technology of Traditional Chinese Medicine Preparation", China Pharmacy, Dec. 31, 2011, pp. 285-287.
"International Search Report (Form PCT/ISA/210)", dated Dec. 19, 2016, with English translation thereof, pp. 1-6.

*Primary Examiner* — Russell G Fiebig
(74) *Attorney, Agent, or Firm* — JCIPRNET

(57) ABSTRACT

A method for extraction of Chinese herbal medicines using a small molecule micro-shear technology, including: pretreating, jet milling, grinding, pulverizing, cell-wall breaking, and extraction of Chinese herbal medicines, so that the raw material can be fully utilized. Herbs are cut into small molecule substances, which is easy to be absorbed by the means of a superfine grinding technology and a cell-wall breaking technology. By means of a supercritical carbon dioxide extraction technology, active ingredients in Chinese herbal medicines can be efficiently and singly extracted, and organic solvent residues in the raw herbs can be removed.

2 Claims, No Drawings

METHOD FOR EXTRACTION OF CHINESE HERBAL MEDICINE USING SMALL MOLECULE MICRO-SHEAR TECHNOLOGY

CROSS-REFERENCE TO RELATED APPLICATION

This application is a 371 application of International PCT application serial no. PCT/CN2016/080467, filed on Apr. 28, 2016, which claims the priority benefit of Chinese application no. 201610190063.3, filed on Mar. 30, 2016. The entirety of each of the abovementioned patent applications is hereby incorporated by reference herein and made a part of this specification.

BACKGROUND

Technical Field

The invention relates to the field of drug extraction, particularly relates to a method for extraction of Chinese herbal medicines using small molecule micro-shear technology.

Description of Related Art

The development of pharmaceutics has experienced four stages: the first generation of preparations is general dosage form, such as capsules, tablets, suppositories, injections, etc.; the second is prodrugs and sustained and controlled release preparations; the third is controlled release preparations; and the fourth is targeted preparations. The development of new pharmaceutics, technologies, processes and excipients are inseparable from the four stages of pharmaceutics development.

At present, the pharmaceutical delivery system, namely the new pharmaceutics of third and the fourth generation, has become an important development direction in the field of pharmacy. The sustained and controlled release drug delivery system, transdermal drug delivery system and targeting delivery system are the mainstream of development and hot spot of research. The specific directions are as follows: the sustained and controlled release drug delivery system: the sustained and controlled release drug delivery system, also known as the sustained and controlled release preparations, which is the fastest growing new drug delivery system. The drug is made into a sustained and controlled release drug delivery system by using sustained and controlled release preparation technology, which can release at a pre-designed rate, and deliver into the body safely and effectively. Comparing to the traditional preparations, the sustained and controlled release drug delivery system can reduce the times of doses and improve the compliance of patients; the sustained and controlled release drug delivery system can also reduce "peaks and valleys" fluctuations in blood concentration and toxic side effects, and improve the efficacy; and it can also increase the stability of the treatment, avoid the irritating effects of certain drugs on the gastrointestinal tract. According to the administration route, the sustained and controlled release preparations have various forms, such as oral sustained and controlled release preparations, injection sustained and controlled release preparations, and implantable sustained-release preparation, etc.

Transdermal drug delivery system: the transdermal drug delivery system refers to a controlled release preparation, which can rapidly penetrate the skin and enter the blood circulation to act as a systemic treatment after transdermal administration. The transdermal drug delivery system has the following unique advantages over the general administration methods, the transdermal drug delivery system can eliminate the "first pass effect" of the liver and the destruction of the gastrointestinal tract, and can be stored in the skin layer, which makes the drug concentration curve more gently, avoiding the "peak valley" and providing a predetermined and long duration of action. The transdermal drug delivery system also can maintain a stable and long-lasting blood concentration, has low toxicity and adverse reactions, and is convenient to use.

Targeting delivery system: using the liposome, nanoparticle, microspheres and other microparticle carriers, ligands or antibody microparticles to target therapeutic drugs to the lesion location, which has little effect on non-target tissues, organs and cells, thereby improving efficacy and reducing the side effects of the drug.

The utilization rate of active ingredients in Chinese herbal medicines has always been a key issue that restricts the efficacy of the above administration routes. The graininess of the Chinese herbal medicines greatly affects the release and the subsequent extraction of the active ingredients in the drugs. Traditional Chinese medicine decoction pieces have a history of application for thousands of years, but they have defects such as inconvenient usage, lagging quality standards, and uneven quality. Scholars from countries and regions with more traditional Chinese medicines such as China, Japan, South Korea and Taiwan have done a lot of exploration and research work on the development of Chinese herbal medicines. Up to now, traditional Chinese medicine decoction pieces have experienced four generations, respectively, traditional Chinese medicine decoction pieces (Chinese medicine decoction pieces collected in "Chinese Pharmacopoeia" or local standards), granular decoction pieces (Japan or domestic and international industrial feeding pieces), single Taste extract granules (Chinese formula granules) and Chinese medicine broken wall pieces (Super Micro Pieces or Taiwanese single-flavored Chinese medicine powder). Traditional Chinese medicine decoction pieces (current Pharmacopoeia or local standards) is one of the main methods of clinical application of TCM, which has thousands of years of application and theoretical understanding. It can add or subtract medicine according to the disease, and it needs to be boiled when used. However, it is easy to have problems of uneven and uncontrollable quality due to the roughness and difference in the form of the medicine, and the method of boiling and taking is cumbersome. The traditional long-time and high-temperature boiling is easy to damage and loss natural active ingredients in the drug. In this way, the raw materials of Chinese medicinal materials can not be fully utilized, resulting in a large amount of waste, and it is also easy to make the dose of the active ingredients in the traditional Chinese medicine preparation unstable.

The efficient extraction of active ingredients is an important prerequisite for the deep processing of Chinese herbal medicines. At present, the extraction technology of Chinese herbal medicines is mainly based on traditional methods such as water extraction alcohol extraction and so on. However, heating, organic solvents, etc. destroy active ingredients to a large extent, such as polypeptides and proteins which are not heat-resistant in Chinese herbal medicines, and the release rate of active substances and the utilization ratio of water-soluble substances in Chinese medicinal materials are significantly lowered. Therefore, the development of the efficient extraction of active ingredients is of great significance for improving the added value of Chinese herbal medicines.

The principle of the supercritical fluid extraction and fractionation process is to utilize the special dissolution of supercritical carbon dioxide for certain special natural products to extract and separate. The solvent strength of the supercritical fluid depends on the temperature and pressure of the extraction. By using this property, it is only necessary to change the pressure and temperature of the extractant fluid, and the different components in the sample can be extracted according to the solubility in the fluid one after another. The weakly polar components are first extracted under low pressure. As the pressure increases, the more polar and large molecular weight components are separated from the basic solute.

The Chinese herbal medicines are directly used for extraction after preparing into the coarse powder through a simple processing process. Due to the large particles and small specific surface area, the active ingredients cannot be fully extracted, the medicinal materials are wasted, and the active ingredients are not comprehensive. The ultrafine pulverization technique or the nanotechnology are subsequently developed, which can process the medicines into ultrafine powders. The Patent Application No. 2009101934934 discloses a method of separating borneol by using the supercritical $CO_2$ fluid extraction system. The method used $CO_2$ as a solvent to dissolve the crude borneol, and a relatively pure borneol product can be isolated. Although the ultrafine pulverization technique has made significant progress compared to traditional technology, its essence is still processed by different physical means. Since the biologically active substance exists in the cells, simple pulverization, no matter how fine, cannot effectively release various active ingredients in the Chinese herbal medicines, and the human body is difficult to effectively absorb and utilize them. Although the physical changes of the particle clusters or molecular groups in the material are beneficial to the dissolution of the active ingredients, the solubility of the active ingredients is not changed. Therefore, the problem of poor water solubility and low bioavailability of some active ingredients has not been fundamentally solved. Therefore, the key to the research of new technology processing technology is to increase the solubility of active ingredients, enhance the water solubility of active materials, and meet the requirements of industrial production.

SUMMARY

In order to solve the problem of the large particle size and the low extraction rate of the Chinese herbal medicines, the poor dissolution of the active ingredient, the large extracted molecules, and the poor bioavailability caused by the difficulty absorption in the external administration mode in the prior art, the present invention provides a method for extraction of Chinese herbal medicines using small molecule micro-shear technology.

A specific embodiment of the present invention is to provide a method for extraction of Chinese herbal medicines using small molecule micro-shear technology, and the specific steps of the method are as follows:
(1) pretreating raw materials of Chinese herbal medicines, which requires the moisture content ≤8.0%;
(2) initially pulverizing the Chinese herbal medicines until it can pass through a 200 mesh sieve;
(3) pulverizing the pulverized medicinal material by a supersonic jet mill, and the gas flow pressure is between 0.1 and 0.8 MPa;
(4) adding bio-auxiliaries and acidic chemical auxiliaries to the pulverized powder, grinding them into a slurry, then filtering and recovering the slurry;
(5) treating the mixture obtained in the step (4) by using an ultra-fine lamination ball mill for 10-15 min;
(6) putting the entrainer and the materials treated by the ultra-fine lamination ball mill into the extraction kettle of the supercritical fluid extractor, and the supercritical fluid flow rate into the extraction kettle is 30-40 L/h, the temperature of the extraction kettle is 40-55° C., and the pressure is 30-32 MPa, the time of extraction with supercritical fluid is 6-7 h;
(7) taking the fluid from the extraction kettle into the middle of the separation column to separate the fluid by the first stage;
(8) taking the fluid passed through the separation column into a stirred first separation kettle to separate it by the second stage;
(9) taking the fluid separated by the first separation kettle enters the stirred second separation kettle.

Preferably, in the step (3), the gas flow pressure is 0.2-0.5 MPa.

Preferably, in the step (4), the amount of the bio-auxiliaries added to the pulverized powder is 2-3 wt % of the powder; and more preferably, the bio-auxiliaries is one or a combination of two or more of pepsin, trypsin and maltase.

Preferably, in the step (4), the amount of the acidic chemical auxiliaries added to the pulverized powder is 1-2 wt % of the powder; and more preferably, the acidic chemical auxiliary is a 65% ethanol solution of oxalic acid.

Preferably, the separation column has a pressure of 10-15 MPa and a temperature of 60-70° C., and the first separation kettle has a pressure of 5-8 MPa and a temperature of 20-55° C., the second separation kettle has a pressure of 5-8 MPa and a temperature of 20-55° C.

The advantages of the invention are:

The effects of micro-shear-auxiliary interaction technology and super-dispersion pulverization technology on extracting Chinese herbal medicines are as follows: The organic solvent for extracting was 65% ethanol at the same extraction conditions, and when the solvent was water, the temperature was set at 64° C. In order to elute the active ingredients sufficiently, the extraction time was selected for 3 hours. The result shows that the extraction effect of the micro-shear-auxiliary interaction technology is significantly better than ultra-fine pulverization technology. And the selection of active substances and auxiliaries in the micro-shear-auxiliary technology extract is very important, which directly affects the extraction effect of the targets. Proper auxiliaries can significantly increase the yield of the target and its solubility in the water.

After the cutting and extraction treatment by the method of the present invention, the effective ingredient in the drug is sufficiently released in the form of small molecules. The drug can be directly applied to the affected area, directly absorbed by transdermal without any carrier, which can be quickly targeted to the affected area.

The extraction process of the present invention is simple, the operation is convenient, and the extraction time is only 20-30 min. Since the amount of organic solvent is reduced during the extraction process, it is more environmentally friendly.

The method of the present invention can greatly improve the extraction rate of the medicinal material, due to the small molecular size of the extracted medicinal materials, the bioavailability is greatly improved, and therefore, the activity is greatly improved, which has a good application prospect.

DESCRIPTION OF THE EMBODIMENTS

Example 1

(1) Pretreating 500 g panax notoginseng raw materials removed of mildew and impurity until the moisture content ≤8.0%.

(2) Initially pulverizing the Chinese herbal medicines material until it can pass through a 200 mesh sieve.

(3) Pulverizing the pulverized medicinal material by a supersonic jet mill, and the gas flow pressure is between 0.1 and 0.8 MPa.

(4) Adding 2-3 wt % of maltase and 1-2 wt % of 65% ethanol solution of oxalic acid to the pulverized powder, grinding them into a slurry, then filtering and recovering the slurry.

(5) Treating the mixture obtained in the step (4) by using an ultra-fine lamination ball mill for 10-15 min.

(6) Putting 120 mL of propylene glycol and the materials treated by the ultra-fine lamination ball mill into the extraction kettle of the supercritical fluid extractor, and the supercritical fluid flow rate into the extraction kettle is 40 L/h, the temperature of the extraction kettle is 52° C., and the pressure is 32 MPa, the time of extraction with supercritical fluid is 7 h.

(7) Taking the fluid from the extraction kettle into the middle of the separation column to separate the fluid by the first stage. The separation column has a pressure of 12 MPa and a temperature of 65° C.

(8) Taking the fluid passed through the separation column into a stirred first separation kettle to separate it by the second stage. The first separation kettle has a pressure of 5.5 MPa and a temperature of 55° C.

(9) Taking the fluid separated by the first separation kettle enters the stirred second separation kettle. The second separation kettle has a pressure of 5 MPa and a temperature of 45° C.

Example 2

(1) Pretreating 500 g pinellia ternate raw materials removed of mildew and impurity until the moisture content ≤8.0%.

(2) Initially pulverizing the Chinese medicinal material until it can pass through a 200 mesh sieve.

(3) Pulverizing the pulverized medicinal material by a supersonic jet mill, and the gas flow pressure is between 0.2 and 0.5 MPa.

(4) Adding 2-3 wt % of trypsin and 1-2 wt % of 65% ethanol solution of oxalic acid to the pulverized powder, grinding them into a slurry, then filtering and recovering the slurry.

(5) Treating the mixture obtained in the step (4) by using an ultra-fine lamination ball mill for 10-15 min.

(6) Putting 120 mL of propylene glycol and 250 g materials treated by the ultra-fine lamination ball mill into the extraction kettle of the supercritical fluid extractor, and the supercritical fluid flow rate into the extraction kettle is 40 L/h, the temperature of the extraction kettle is 52° C., and the pressure is 32 MPa, the time of extraction with supercritical fluid is 7 h.

(7) Taking the fluid from the extraction kettle into the middle of the separation column to separate the fluid by the first stage. The separation column has a pressure of 12 MPa and a temperature of 65° C.

(8) Taking the fluid passed through the separation column into a stirred first separation kettle to separate it by the second stage. The first separation kettle has a pressure of 5.5 MPa and a temperature of 55° C.

(9) Taking the fluid separated by the first separation kettle enters the stirred second separation kettle. The second separation kettle has a pressure of 5 MPa and a temperature of 45° C.

Test Example 1

The forsythia was extracted by the method of Example 1 of the present invention and the method of Example 1 of Patent No. 2009101934934 (Control), and the therapeutic effects of both on the swelling of the ear shell skin of the mouse were examined. The experimental steps are as follows:

Experimental principle: Using inflammatory agents to cause swelling of the ear skin, and the weight of the inflamed ear shell of the applied medicine group and the control group was observed and measured, and the difference in swelling rate was compared.

Operation Method:

(1) Male mice of 25 to 30 g were used.

(2) Under anesthesia of ether, about 0.1 mL the mixed pro-inflammatory solution was applied to both sides of the left ear of the mouse (The inflammation solution contains 2% croton oil, 20% pyridine, 5% distilled water and 73% diethyl ether). The right ear is used as a control.

(3) 0.03 mL/kg of test drug was injected intraperitoneally 0.5-1 hour before the inflammation.

(4) After 4 h, the mice were sacrificed, and the ears were cut. The original ear pieces were taken off with a 9 mm diameter puncher on the same part, and weighed with a balance. The weight of the left ear piece per mouse minus the weight of the right ear piece is the degree of swelling. The mean value and standard deviation of the swelling degree of each group were calculated, and the swelling inhibition rate of the administration group was determined according to the formula. The formula is: swelling rate a=(inflamed ear weight−uninflamed ear weight)/uninflamed ear weight.

(5) Both the applied drug and the control group were diluted to 1%.

The experimental results are as follows:

| Drug | Number of animals | Swelling rate |
| --- | --- | --- |
| Example 1 | 20 | 0.67 ± 0.05 |
| Example 2 | 18 | 0.73 ± 0.09 |
| Control group | 18 | 1.62 ± 0.12 |

From the above results, it was found that the swelling rates of the mouse ear pieces prepared by the method of the present invention were all lower than that of the control group. The pulverization and extraction method of the present invention allows the effective ingredients in the Chinese herbal medicines to be completely retained and fully utilized, so that the obtained drug has a remarkable effect.

The detailed description of the present invention is intended to be illustrative of the preferred embodiments of the present invention, and is not intended to limit the scope of the present invention. Equivalent implementation or modification without departing from the invention shall be included in the scope of the technical scheme of the invention.

What is claimed is:

1. A method for extraction of Chinese herbal medicines using small molecule micro-shear technology, comprising:
   (1) pretreating 500 g forsythia raw materials removed of mildew and impurity until the moisture content ≤8.0%;
   (2) initially pulverizing the Chinese herbal medicinal material until it can pass through a 200 mesh sieve;
   (3) pulverizing the pulverized medicinal material by a supersonic jet mill, and a gas flow pressure is between 0.1 and 0.8 MPa;
   (4) adding 2-3 wt % of maltase and 1-2 wt % of 65% ethanol solution of oxalic acid to a pulverized powder, grinding them into a slurry, then filtering and recovering the slurry;
   (5) treating a mixture obtained in the step (4) by using an ultra-fine lamination ball mill for 10-15 min;
   (6) putting 120 mL of propylene glycol and materials treated by the ultra-fine lamination ball mill into an extraction kettle of a supercritical fluid extractor, and the supercritical fluid flow rate into the extraction kettle is 40 L/h, the temperature of the extraction kettle is 52° C., and the pressure is 32 MPa, the time of extraction with supercritical fluid is 7 h;
   (7) taking the fluid from the extraction kettle into middle of a separation column to separate the fluid by a first stage, wherein the separation column has a pressure of 12 MPa and a temperature of 65° C.;
   (8) taking the fluid passed through the separation column into a stirred first separation kettle to separate it by a second stage, wherein the first separation kettle has a pressure of 5.5 MPa and a temperature of 55° C.; and
   (9) taking the fluid separated by the first separation kettle enters a stirred second separation kettle, wherein the second separation kettle has a pressure of 5 MPa and a temperature of 45° C.

2. The method for extraction of Chinese herbal medicines using small molecule micro-shear technology of claim 1, wherein the gas flow pressure is 0.2-0.5 MPa.

* * * * *